United States Patent
Honda et al.

(10) Patent No.: US 7,181,060 B2
(45) Date of Patent: Feb. 20, 2007

(54) DEFECT INSPECTION METHOD

(75) Inventors: Toshifumi Honda, Ebina (JP); Hirohito Okuda, Yokohama (JP); Yasuhiko Ozawa, Abiko (JP); Katsuhiro Kitahashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 984 days.

(21) Appl. No.: 10/081,782

(22) Filed: Feb. 20, 2002

(65) Prior Publication Data
US 2003/0015659 A1 Jan. 23, 2003

(30) Foreign Application Priority Data
Jul. 18, 2001 (JP) .............................. 2001-217510

(51) Int. Cl.
*G06K 9/00* (2006.01)
(52) U.S. Cl. ..................................... 382/151
(58) Field of Classification Search ................ 382/141, 382/143–152; 356/237.1, 237.4, 237.5; 348/87, 348/126
See application file for complete search history.

(56) References Cited

U.S. PATENT DOCUMENTS 5,659,172 A * 8/1997 Wagner et al. .............. 250/307
6,947,587 B1 * 9/2005 Maeda et al. ............... 382/149
6,965,429 B2 * 11/2005 Honda et al. ............. 356/237.1

FOREIGN PATENT DOCUMENTS

JP 01-143127 6/1989

OTHER PUBLICATIONS

Berhold Klaus Paul Horn, "Reflectance Map: Shape from Shading," *Robot Vision* (1986), The MIT Press (Boston), pp. 245-277.

* cited by examiner

*Primary Examiner*—Vikkram Bali
(74) *Attorney, Agent, or Firm*—Townsend and Townsend and Crew LLP

(57) ABSTRACT

An image picked up by a detection system capable of actualizing a three-dimensional inclination is usually poor in the signal-to-noise ratio, and it is difficult to stably detect minute defects. Images that actualize a three-dimensional inclination are picked up from opposed directions. The images are subject to subtraction and addition. The images improved in signal-to-noise ratio as compared with original images are calculated. The images calculated and improved in signal-to-noise ratio respectively of a defect portion and a reference portion are compared with each other. Regions differing in comparison results are detected as defects. As a result, minute defects can be inspected stably.

13 Claims, 7 Drawing Sheets

DEFECT INSPECTION METHOD

BACKGROUND OF THE INVENTION

The present invention relates to a defect inspection method, and in particular to a defect inspection method of semiconductor products that requires defect inspection of high precision.

As the semiconductor design rule becomes finer, the size of manufacturing defects of semiconductor products becomes extremely small. For observation of semiconductor defects, scanning electron microscopes (hereafter referred to as SEMs) have begun to be used besides conventional optical microscopes. However, secondary electrons typically detected in SEMs have a problem that images with edges emphasized are often picked up and defects cannot be necessarily actualized favorably.

Therefore, a technique of detecting reflected electrons together with secondary electrons are detected and detecting a defect by using both detected signals complementarily has begun to be applied. Since reflected electrons emitted from the inspection subject has a directivity, an output correlated with an inclination of a three-dimensional slope in a position of electron beam irradiation is obtained and it can also be utilized for obtaining a defect shape.

It is known that the method utilizing reflected electrons is effective in detecting defects. For example, in a technique disclosed in U.S. Pat. No. 5,659,172, defects are extracted by detecting perspective images from a plurality of different directions in each of inspection positions and reference positions corresponding to the inspection positions, comparing perspective images detected from the same direction in an inspection position and a reference position, creating a plurality of comparison maps, and conducting computation on comparison maps.

However, the conventional technique has a problem that comparison maps created by comparing perspective views are susceptible to noise, and consequently minute defects cannot be detected stably. As the method for detecting perspective images, a technique of detecting only electrons emitted from a subject into a certain narrow angle direction by applying an electron beam to an imaging subject is typical.

As compared with the case where the angle is not restricted, the electron detection intensity becomes small, and consequently the signal-to-noise ratio of the perspective views is aggravated. When comparing perspective images picked up in a defect position and a reference position at high magnification, local perturbation is usually applied in many cases in order to allow manufacturing tolerance of non-defective portions. It is now supposed that two images, i.e., an image 1 and an image 2 are compared with each other in local perturbation. When an evaluation pixel in the image 1 is compared with a reference pixel in the image 2 corresponding thereto, a region corresponding to the manufacturing tolerance around the reference pixel in the image 2 is set. A difference between the evaluation pixel value and a pixel value that is closest to the evaluation pixel value among all pixels in the set region is outputted as a difference in the inspection pixel between the image 1 and the image 2.

This algorithm has a problem that when the signal-to-noise ratios of compared images are poor, a signal component of an obtained output image remarkably lowers. Because of this problem, there is a tendency to overlook minute defects in a high magnification state.

SUMMARY OF THE INVENTION

The problem of the conventional technique is solved by a defect inspection method including the steps of picking up images of a sample from a plurality of directions, thereby obtaining external appearance images of an inspection subject region of the sample picked up from the plurality of directions; picking up images of a comparison subject region designed so as to originally have an external appearance identical with that of the inspection subject region of the sample from a plurality of directions identical with those of the inspection subject region, thereby obtaining external appearance images of the comparison subject region picked up from the plurality of directions; correcting mis-registrations between the external appearance images of the inspection subject region of the sample picked up from the plurality of directions and the external appearance images of the comparison subject region picked up from the plurality of directions that respectively correspond to the external appearance images of the inspection subject region picked up from the plurality of directions; and detecting defects of the inspection subject region by using the external appearance images of the inspection subject region of the sample picked up from the plurality of directions and the external appearance images of the comparison subject region picked up from the plurality of directions corrected in mis-registration.

Other objects, features and advantages of the invention will become apparent from the following description of the embodiments of the invention taken in conjunction with the accompanying drawings.

DESCRIPTION OF THE EMBODIMENTS

The present invention will now be described by referring to FIGS. 1 to 7.

Figure 1:
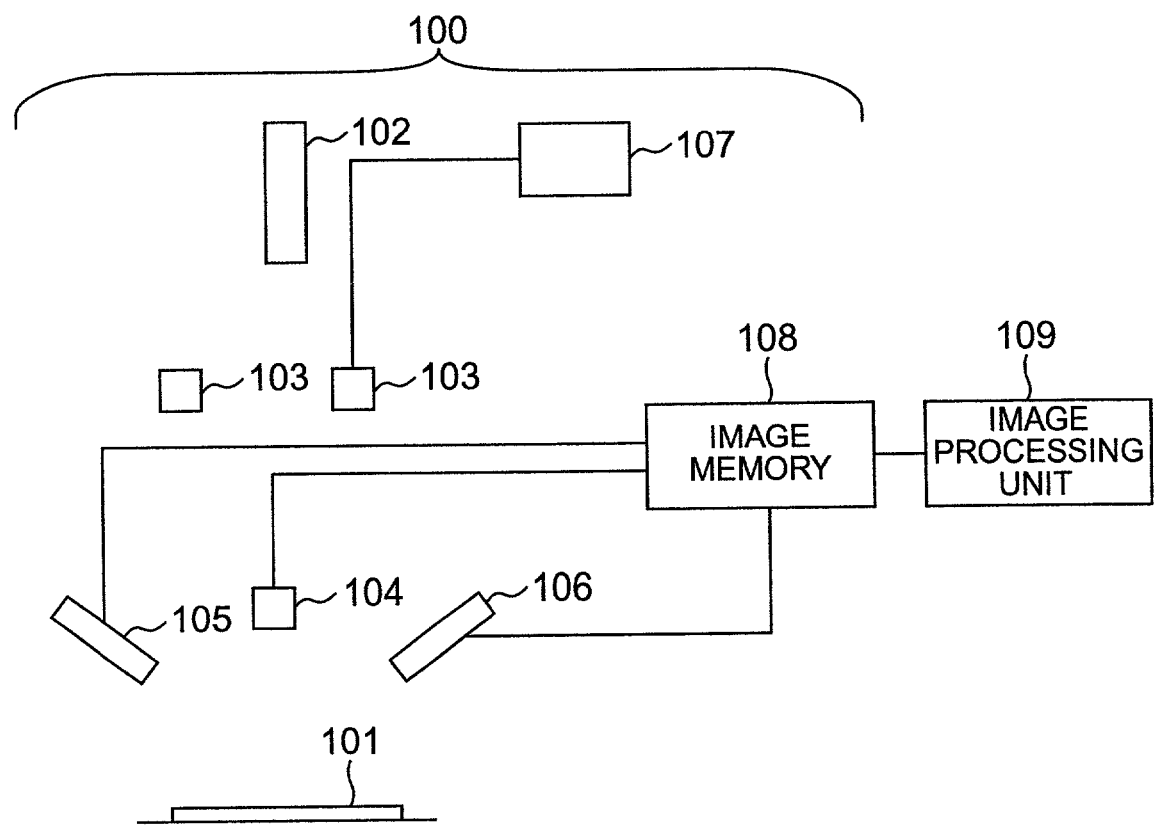
FIG. 1 is a basic configuration diagram of an embodiment according to the present invention.

FIG. 1 is a block diagram showing a schematic general configuration of a semiconductor defect analysis system that is an embodiment of the present invention. Numeral 101 denotes an inspection subject. Numeral 100 denotes an image pickup unit, which includes basic components 102 to 108 described hereafter. Numeral 102 denotes an electron gun for applying electrons to the inspection subject 101 via an electron scanning unit 103. Numeral 104 denotes a non-directional electron detection unit for detecting secondary electrons and reflected electrons generated from a sample by irradiation of electrons. Numerals 105 and 106 denote narrow angle electron detection units for detecting secondary electrons and reflected electrons coming from a certain narrow angle direction range among secondary electrons and reflected electrons generated from the sample by irradiation of electrons. The narrow angle electron detection units 105 and 106 are designed so as to be different in narrow angle electron detection direction rage. The electron scanning unit 103 is controlled by a controller 107 so that two-dimensional scanning will be conducted with electrons emitted from the electron gun 102. Numeral 108 denotes an image memory for storing outputs of the detection units 104, 105 and 106. Since two-dimensional scanning is conducted with electrons by the electron scanning unit 103, defect images which differ in property according to the detection unit are stored in the image memory 108.

Figure 2:
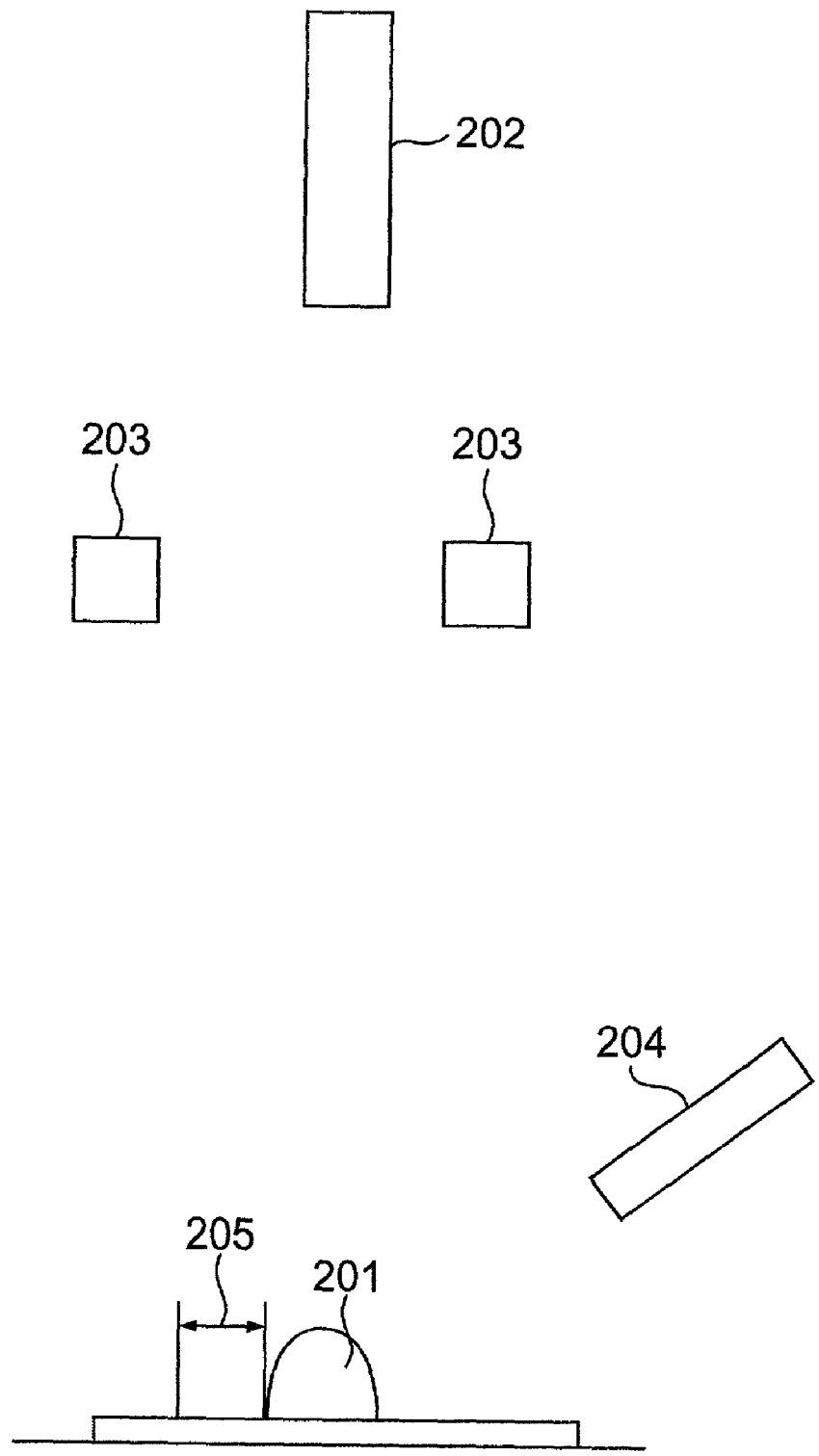
FIG. 2 is a diagram showing an image feature in an embodiment according to the present invention.

The property of a narrow electron image will now be described by referring to FIG. 2. Numeral 201 denotes a sectional shape of a defect that has stuck to the inspection subject. Numeral 202 denotes the electron gun. Numeral 203 denotes the electron scanning unit. Numeral 204 denotes the electron detection unit for detecting electrons from a narrow angle direction. The electron detection unit 204 detects electrons reflected at the surface of the defect. When the defect surface is perpendicular to a line connecting the defect 201 and the electron detection unit 204, the electron detection unit 204 obtains a strong signal. On the contrary, when the defect surface is in parallel to the line connecting the defect 201 and the electron detection unit 204, the electron detection unit 204 obtains a weak signal. In the case where electrons are detected from opposed directions as represented by 105 and 106 shown in FIG. 1, a slope detected brightly in an image detected by the detection unit 105 is detected darkly by the detection unit 106, and on the contrary a slope detected darkly in an image detected by the detection unit 105 is detected brightly by the detection unit 106. Numeral 205 in FIG. 2 denotes a shadow region of the defect 201. The region 205 is a region having no inclination, but the adjacent defect becomes an obstacle. Since electrons from the surface of the region 205 do not arrive at the electron scanning unit 203 sufficiently, the region 205 is detected darkly.

Owing to the property heretofore described, the inclination of the detection subject can be actualized by using a two-dimensional image formed from a signal obtained by the narrow angle electron detection units. Because of this property, images obtained from detection conducted by the narrow angle electron detection units 105 and 106 are hereafter referred to as perspective image 1 and perspective image 2, respectively.

For conducting a review of semiconductor defects, it is necessary to extract defects. A technique for extracting defects most easily is pattern comparison. That is, it becomes possible to identify a region of a defect by comparing the defect with a semiconductor pattern of a non-defective article formed by the same design as that of the position of the defect. In order to implement this, a defect pattern containing a picked-up defect image and a reference pattern containing no defects are preserved in the image memory 108. Each of the defect pattern and the reference pattern is formed of the non-directional electron image, the perspective image 1 and the perspective image 2. Hereafter, sets each having three images are referred to as defect image set and reference image set.

Numeral 109 denotes an image processing unit, which compares a defect image stored in the image memory 108 with a reference image to extract defects. The image memory 108 provided on the image pickup unit 100 and image processing unit 109 may be connected to each other in a hardware manner or may be connected to each other via communication means such as a line. In the case where they are connected via communication means via a line, the image processing unit 109 can be installed at a distance from the image pickup unit 100 having the image memory 108.

Figure 3:
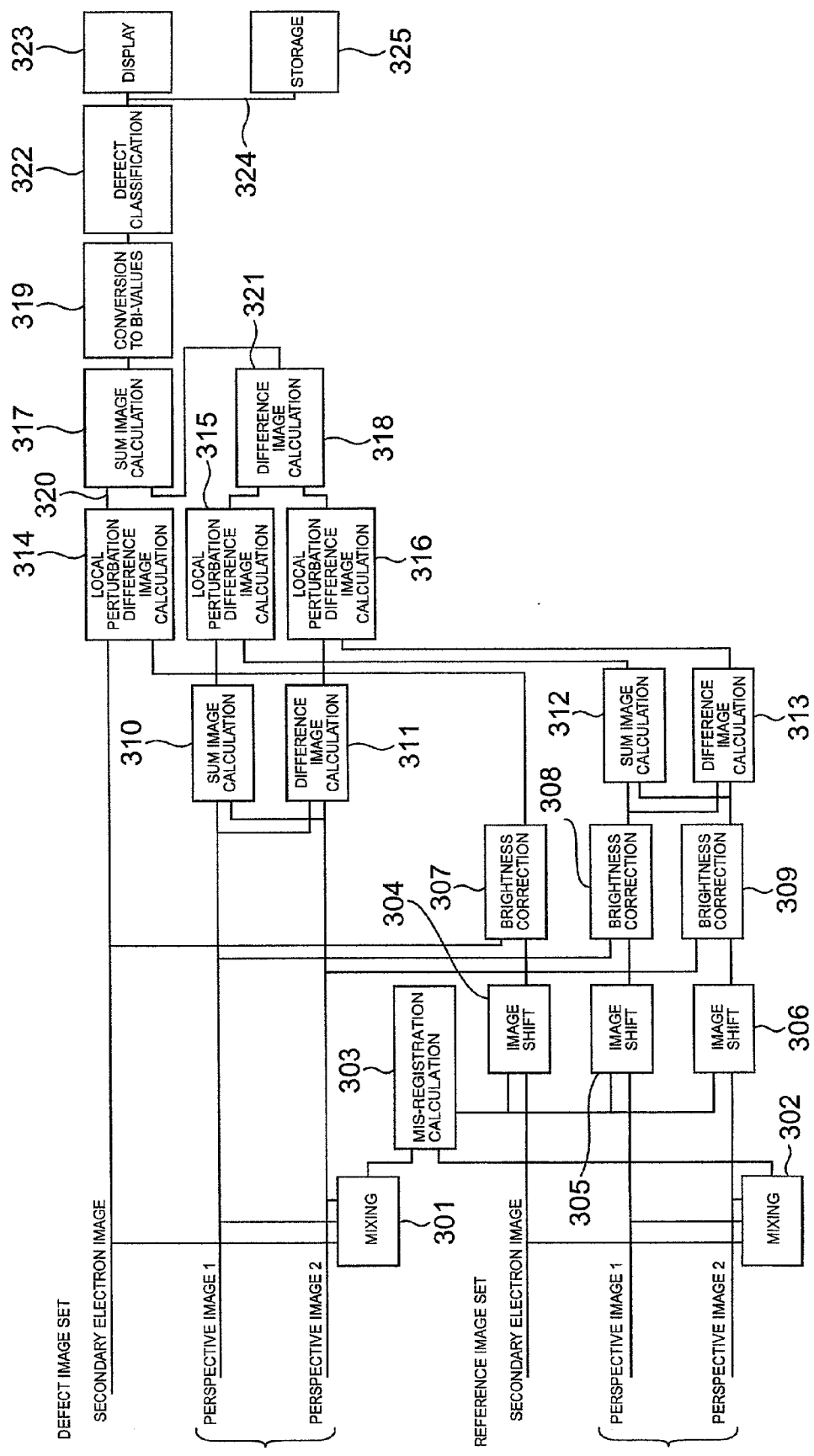
FIG. 3 is a diagram showing an embodiment of a defect extraction method according to the present invention.
Figure 4:
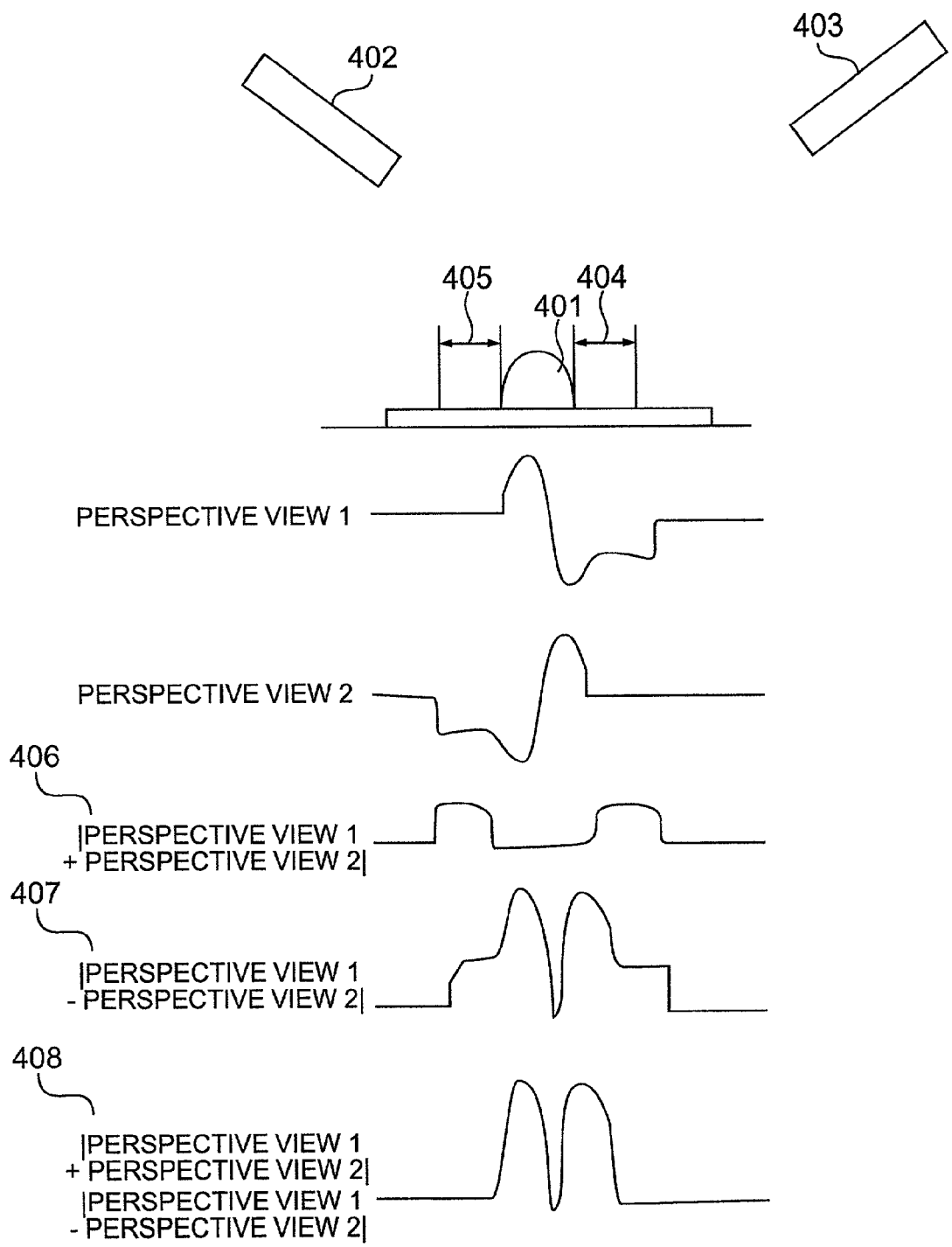
FIG. 4 is a diagram showing an image feature in an embodiment according to the present invention.

FIG. 3 shows defect extraction steps. First, three images obtained from the image pickup units 104, 105 and 106 are mixed by computation (301 and 302) to generate one image. This computation is conducted for each of the defect image set and the reference image set. As a result, two mixed images are calculated. As for the perspective images 1 and 2, it is desirable to obtain a difference. The reason will now be described by referring to FIG. 4. Numeral 401 denotes an inspection subject. Numerals 402 and 403 denote electron detection units installed so as to be opposed to each other. Numeral 404 denotes a region that has become a shadow because the inspection subject 401 itself becomes an obstacle when the detection unit 402 detects electrons and electrons cannot be detected sufficiently. Numeral 405 denotes a region that has become a shadow for the same reason when the detection unit 403 detects electrons. The detection units 402 and 403 detect electrons coming from opposite directions. This results in the following property. Typically, a region detected brightly by the detection unit 402 is detected darkly by the detection unit 403, and on the contrary, a region detected darkly by the detection unit 402 is detected brightly by the detection unit 403. When signals of the detection units 402 and 403 detected in the same position are represented by a two-dimensional vector, distribution of this vector in different positions is subject to main component analysis. It will be appreciated that the main component becomes nearly the difference of signals of the regions 402 and 403 because of the above-described property. Therefore, it will be appreciated that it is effective to calculate the difference between the perspective image 1 and the perspective image 2 in order to reduce the loss of information when three images are combined into one image.

One image is calculated from three images by calculating the difference between the perspective images and adding the non-directional electron image to the difference. By thus obtaining one image, it becomes possible to implement registration between the defect image set and the reference image set at a time. In the external view of the inspection subject, there are both portions that are easy to be picked up in a perspective image with high contrast and portions that are easy to be picked up in the non-directional image with high contrast. By combining high information content components of three images, which are different in property, into one image, it is possible to implement registration with higher precision as compared with the case where each image is registered singly.

Subsequently, a mis-registration quantity between the obtained defect image set and the reference image set is derived (303). In order to correct the derived mis-registration quantity, image shifts of the reference image set (304 to 306) are conducted.

In addition, in order to make equal in brightness corresponding images between the defect image set and the reference image set corrected in mis-registration, brightness corrections (307 to 309) are conducted.

Successively, in each of the defect image set and the reference image set, a sum image and a difference image of the perspective image 1 and the perspective image 2 are calculated (310 to 313). Between the defect image set and the reference image set, difference images respectively of the sum image and the difference image are calculated by using local perturbation (314 to 316). Pre-dominance of deriving difference images and sum images once and thereafter calculating local perturbation difference images over direct calculating local perturbation difference images of the perspective view 1 and the perspective view 2 of the defect image set and the reference image set will now be described by referring to FIG. 5. The difficulty at the time when extracting defects by using perspective images lies in the fact that signal components are greater than noise components in perspective images. Since the perspective image detector detects only electrons coming from a narrow angle direction range, the signal-to-noise ratio tends to fall as compared with the ordinary non-directional electron image.

Figure 5:
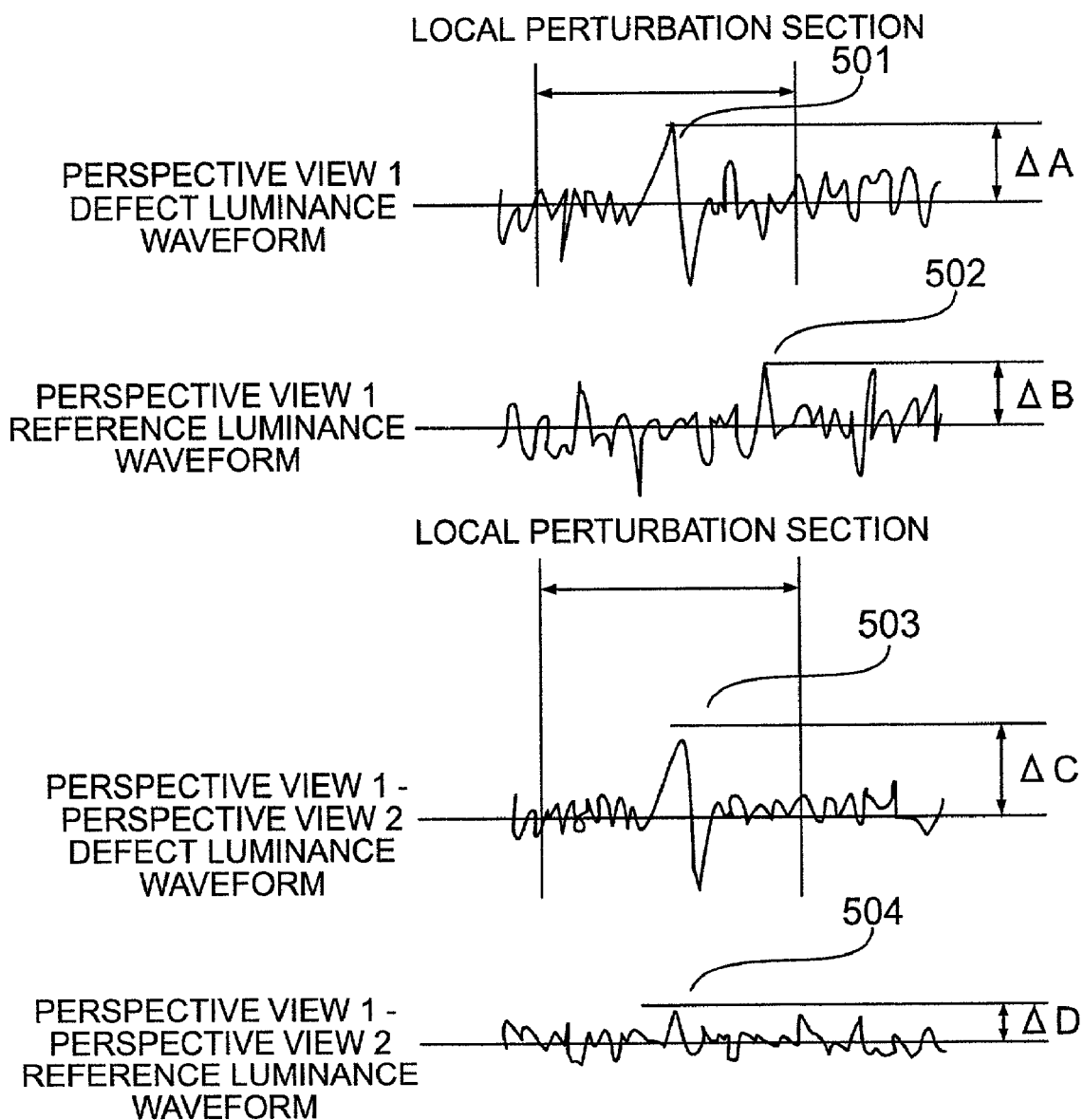
FIG. 5 is a diagram showing a signal-to-noise ratio improving method in defect extraction processing according to the present invention.

On the other hand, when defects at high magnification are detected, the pixel size tends to become small with respect to the manufacturing tolerance of the pattern to be inspected. Therefore, a necessity to calculate local perturbation difference image occurs. In the local perturbation difference image calculation, a section of a certain fixed region centering around an inspection pixel is set as a local perturbation region as shown in FIG. 5, a reference pixel that is closest in pixel value to the inspection pixel in this region is specified as a reference pixel corresponding to the inspection pixel. By thus deriving correspondence relations between the inspection image and the reference image every pixel and then subtracting corresponding pixel values, a difference image is generated. As the local perturbation region becomes wide in the local perturbation difference image calculation (314 to 316), the amplitude between the maximum value and the minimum value of noise in the region also becomes large. As a result, there occurs a problem that the difference image signal, i.e., $\Delta A - \Delta B$ in FIG. 5 becomes small.

This problem is improved by increasing the signal-to-noise ratio. Noise superposed on the perspective image 1 and the perspective image 2 can be considered to be white noise. In the case where the perspective image 1 and the perspective image are subjected to addition or subtraction, the amplitude is expected to typically become 1.7 times. On the other hand, the amplitude of the signal components is nearly doubled by the subtraction as represented by a waveform 406 of FIG. 4. On the contrary, the pixel value of the slope portion of the subject becomes nearly 0 (zero) as represented by 405. The influence of noise on the local perturbation difference appears generally as lowering of the signal strength. In the case where the inclination of the subject has become nearly 0 (zero) as a result of addition, demerits caused by lowering of the signal strength almost disappear. In the case where subtraction has been conducted, an increase of the signal strength is greater than that of noise, and consequently the signal-to-noise ratio is increased. As represented by the waveform 406 after subtraction, a region extracted in the case where the subtraction has been conducted includes both the defect portion and its shadow portion.

What is needed as a defect is a region of the defect itself, and it is not the shadow portion of the defect. Therefore, it becomes necessary to subtract the shadow region from the waveform 406. This subject is implemented by subtracting the waveform 405 from the waveform 406. In the case where this processing is not conducted, the shadow of the defect is detected together with the defect. In the embodiment described by referring to FIG. 3, the method of subtracting the waveform 405 from the waveform 406 has been described. In the case where only detection of an approximate position of the defect is necessary, it is also possible to omit this processing. As processing which needs only detection of an approximate position of the defect, for example, processing of picking up an image of a defect first at low magnification and calculating its approximate position as pre-processing with respect to processing of observing the defect at high magnification can be mentioned. This processing is frequently needed in Review SEMs.

As for the defect and reference non-directional electron images as well, a difference image is calculated by using local perturbation. A resultant difference image 320 and a defect-reference difference image 321 obtained from the perspective images are added up. A resultant sum image is converted to binary values, and defects are extracted. The extracted defects are classified (322) into preset categories according to feature quantities of defects, and a result is displayed (323) on the screen. The classified defect information (324) is stored (325) in a server or the like via a communication line. By the way, higher defect extraction performance can be implemented by providing the non-directional defect-reference difference image 320 and the perspective defect-reference difference image 321 with appropriate gains before carrying out addition computation. In some inspection subjects, irregular unevenness is present on the surface although the subject has no defects.

In perspective images, even small unevenness generates a large signal when the inclination is large. In the inspection subject having unevenness, therefore, a problem of a false report that normal portions are extracted as defects is caused. By making the gain of the non-directional defect-reference difference image 320 larger than the gain of the perspective defect-reference difference image 321 for such inspection subjects, it becomes possible to extract only defects without being affected by minute unevenness of non-defective portions. On the contrary, when minute unevenness as detected, such as micro-scratches often generated after the CMP process in the semiconductor manufacturing process, the gain of the perspective defect-reference difference image 321 is to be made larger than the gain of the non-directional defect-reference difference image 320.

Although the scheme for extracting defects by utilizing two perspective images has been shown in FIG. 3, it is also possible to detect defects more stably by utilizing more perspective images. For example, it is supposed that there are four perspective images and two perspective images detect electrons in each of mutually contradictory narrow angle direction ranges. In this case, it is possible to consider that there are two corresponding sets each including two perspective images. Therefore, it is conceivable to calculate a signal corresponding to the perspective defect-reference difference image 321 of FIG. 3 from each of the sets and calculate a sum of resultant signals. Since noise components can be considered to be non-correlative in each set, it becomes possible to improve the signal-to-noise ratio by calculating the sum.

As another method of favorably extracting defects by using perspective images without being ago affected by minute unevenness, three-dimensional shape comparison can be mentioned. As for a technique for calculating the three-dimensional shape of the inspection subject on the basis of perspective images, for example, the product of the sum image and the difference image of perspective images becomes the inclination. It is possible to derive the three-dimensional shape as integral of the inclination. Application of smoothing filtering on the image obtained as a product of the sum image and the difference image in a direction parallel to a straight line connecting two narrow angle electron detection units can be regarded as an approximate shape change in a section where convolution of the filter is conducted. A resultant image is referred to as shape image.

Figure 6:
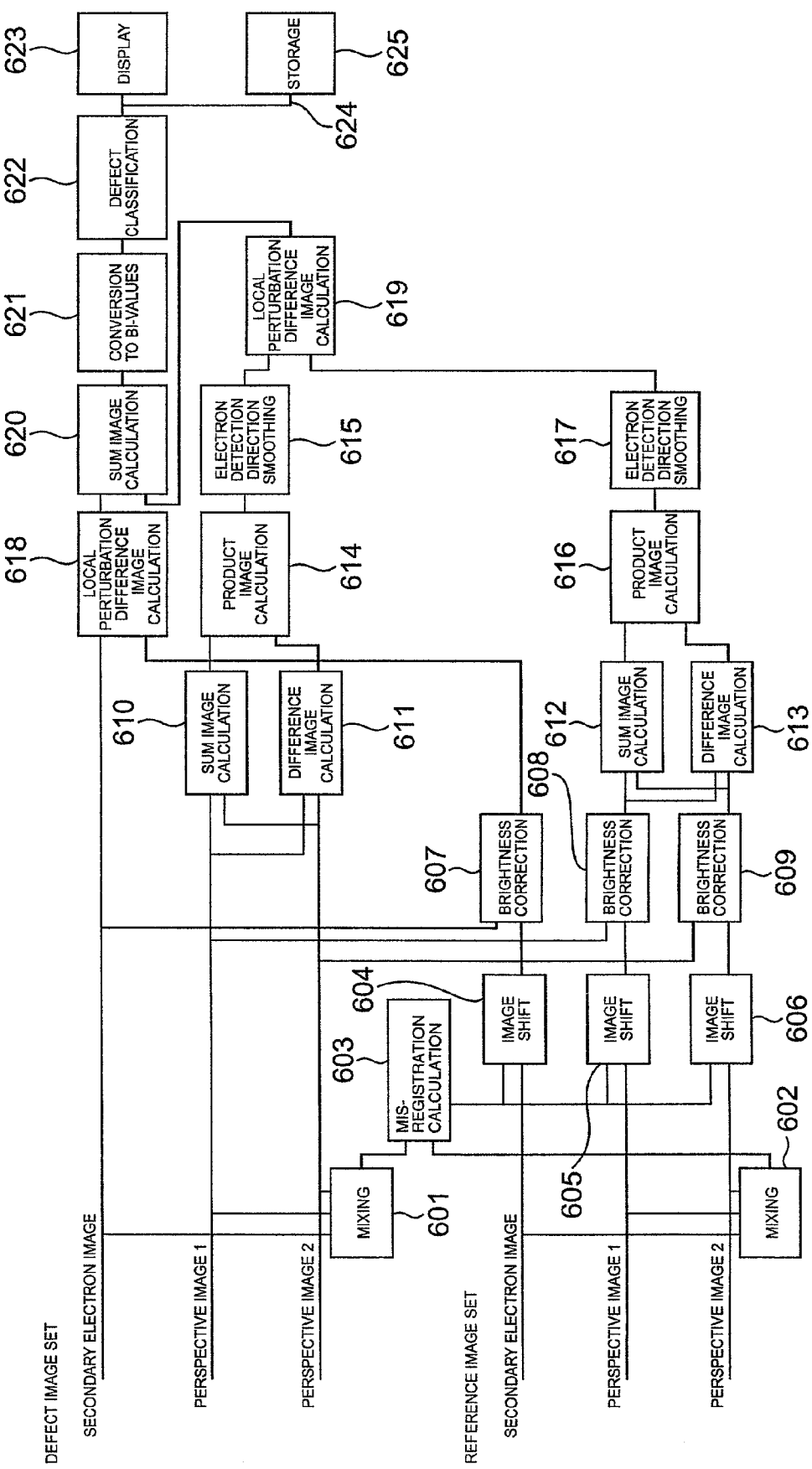
FIG. 6 is a diagram showing an embodiment of a defect extraction method according to the present invention.

A technique for extracting defects on the basis of a three-dimensional shape is shown in FIG. 6.

The configuration of FIG. 6 is same as the configuration of FIG. 3 as far as sum images (610 and 612) and difference images (611 and 613) are calculated from perspective images 1 and 2 of a defect image set and perspective images 1 and 2 of a reference image set. However, an inclination of a defect is derived by calculating (614 and 615) the product of the difference image and the sum image. Typically, in the case where the signal-to-noise ratio of an image is poor, the image becomes less susceptible to an influence of inclination dispersion of the local subject and the extraction performance can be improved by lengthening a smoothing section. When the smoothing section is made too long, the image also tends to be more susceptible to an influence of an offset variation or the like of the image between the defect image set and the reference image set. By calculating (619) a difference image of images after being subjected to smoothing processing (615 and 617), height variations are compared between the defect image set and the reference image set. An absolute value thereof and an absolute value of a difference image (618) of the secondary electron image between the defect image set and the reference image set are added up. A resultant image (620) is converted to bi-values (621). As a result, it becomes possible to extract defects.

By deriving a difference between shape images calculated respectively from the defect image set and the reference image set, stable defect extraction that is not affected by minute unevenness can be implemented. As a matter of course, it is also possible to derive the difference image of the shape image and thereafter adding the difference image of the non-directional electron image. Information of the extracted defects is classified (622) into preset categories according to feature quantities of defects. A result of classification is displayed (623) on the display screen. In addition, the classified defect information (624) is stored (625) in a server via a communication line.

Heretofore, the technique of generating a shape image from two perspective images has been described. It is also possible to form a shape image from more perspective images. For example, as a technique for forming a three-dimensional shape from four perspective images, the technique disclosed in JP-A-1-143127 can be applied.

Figure 7:
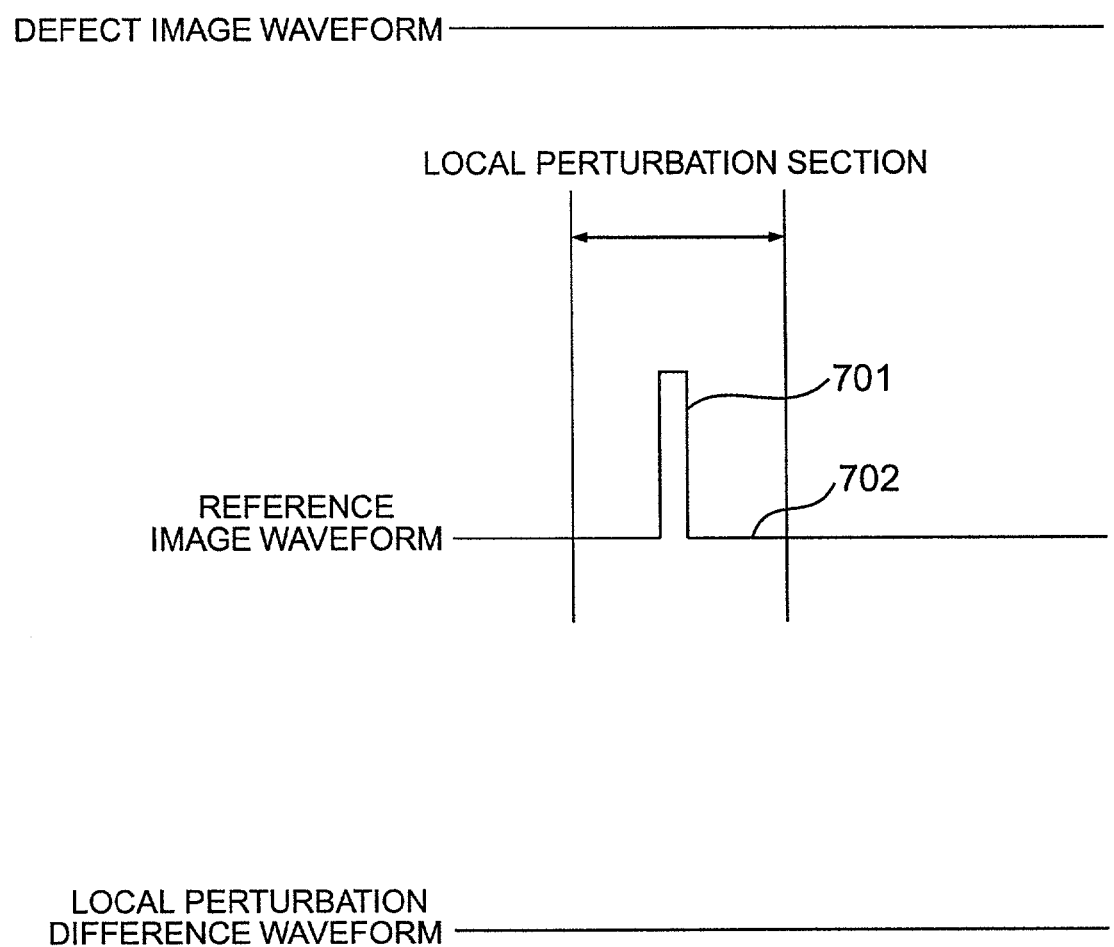
FIG. 7 is a diagram showing an embodiment of an image comparison method according to the present invention.

A technique for generating the difference image will now be described. In the case where the image of the inspection subject is picked up at such a magnification that the pixel size is greater than the size tolerance of the inspection subject as described above, it is necessary to derive an image difference by using local perturbation. This scheme has a problem that defects cannot be extracted in some cases such as the case where a pattern that is to be originally present is not formed. An example thereof is shown in FIG. 7. In the defect image waveform of FIG. 7, a circuit pattern 701 that is to be originally present is not formed. The defect image waveform always has the same luminance value as a flat waveform 702. In the local perturbation, a pixel having luminance closest to the inspection pixel value in the local perturbation section is derived from the reference image, and the luminance difference is outputted as a difference image pixel value.

In the example of FIG. 7, a pixel having the same pixel value as a defect pixel in a position where a circuit is not formed lies in the local perturbation section. Therefore, a defect that the circuit is not formed is overlooked.

For solving this problem, each of local perturbation based on the defect and local perturbation based on the reference is to be conducted once and a greater output of them is to be outputted as a difference image value.

In the embodiment of FIG. 1, the example in which irradiation and detection of the electron beam are conducted has been described. However, similar processing can also be implemented by using light. As a technique for deriving a three-dimensional inclination of the subject from light, there is a technique described, for example, in "Shape from Shading", Berthold Klaus Paul Horn: Robot Vision, MIT Press, pp. 243–277. Without losing the generality, the technique described above can be applied intactly.

By applying the defect detection method heretofore described, subtraction and addition are conducted on perspective images each having a poor signal-to-noise ratio every two perspective images. Thus, images each having a high signal-to-noise ratio are generated. In addition, non-directional images each having a high signal-to-noise ratio are also added. As a result, stable defect detection can be implemented.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspection method comprising the steps of:
applying a focused electron beam onto a sample and conducting scanning;
detecting secondary electrons generated from an inspection subject region of said sample at the focused electron beam applying step by using detectors installed in a plurality of directions, thereby obtaining external appearance images of the inspection subject region of said sample picked up from the plurality of directions;
picking up images of a comparison subject region designed so as to originally have an external appearance identical with that of the inspection subject region of said sample from a plurality of directions identical with those of the inspection subject region, thereby obtaining external appearance images of the comparison subject region picked up from the plurality of directions;
correcting mis-registrations between the external appearance images of the inspection subject region of said sample picked up from the plurality of directions and the external appearance images of the comparison subject region picked up from the plurality of directions that respectively correspond to the external appearance images of the inspection subject region picked up from the plurality of directions; and
detecting defects of the inspection subject region by using the external appearance images of the inspection subject region of said sample picked up from the plurality of directions and the external appearance images of the comparison subject region picked up from the plurality of directions corrected in mis-registrations, wherein the step of correcting the mis-registrations comprises the substeps of:
mixing two perspective images obtained by picking up an image of the inspection subject region of said sample from each of two opposed directions with a non-directional electron image, thereby synthesizing a first mixed image;

mixing two perspective images obtained by picking up an image of the comparison subject region of said sample from each of the two opposed directions with a non-directional electron image, thereby synthesizing a second mixed image; and comparing the first mixed image with the second mixed image, thereby obtaining mis-registration quantities respectively between the two perspective images and the non-directional electron image of the inspection subject region of said sample and the two perspective images and the non-directional electron image of the comparison subject region.

2. The defect inspection method according to claim 1, wherein the step of synthesizing the first mixed image comprises the substep of using information of a difference image between two perspective images obtained by picking up an image of the inspection subject region of said sample from each of two opposed directions, and the step of synthesizing the second mixed image comprises the substep of using information of a difference image between two perspective images obtained by picking up an image of the comparison subject region from each of two opposed directions.

3. A defect inspection method comprising the steps of:

applying a focused electron beam onto a sample and conducting scanning;

detecting secondary electrons generated from an inspection subject region of said sample at the focused electron beam applying step by using detectors installed in a plurality of directions, thereby obtaining external appearance images of the inspection subject region of said sample picked up from the plurality of directions;

picking up images of a comparison subject region designed so as to originally have an external appearance identical with that of the inspection subject region of said sample from a plurality of directions identical with those of the inspection subject region, thereby obtaining external appearance images of the comparison subject region picked up from the plurality of directions;

correcting mis-registrations between the external appearance images of the inspection subject region of said sample picked up from the plurality of directions and the external appearance images of the comparison subject region picked up from the plurality of directions that respectively correspond to the external appearance images of the inspection subject region picked up from the plurality of directions; and detecting defects of the inspection subject region by using the external appearance images of the inspection subject region of said sample picked up from the plurality of directions and the external appearance images of the comparison subject region picked up from the plurality of directions corrected in mis-registrations, wherein the step of detecting defects of the inspection subject region comprises the substeps of:

using information of a difference image of two perspective images obtained by picking up an image of the inspection subject region of said sample from each of two opposed directions; and using information of a difference image two perspective images obtained by picking up an image of the comparison subject region from each of two opposed directions.

4. A defect inspection method according to claim 3, further comprising the step of classifying the detected defects by processing the defect region.

5. A defect inspection method comprising the steps of:

applying a focused electron beam onto a sample and conducting scanning;

detecting secondary electrons generated from an inspection subject region of said sample at the focused electron beam applying step by using detectors installed in a plurality of directions, thereby obtaining external appearance images of the inspection subject region of said sample picked up from the plurality of directions;

picking up images of a comparison subject region designed so as to originally have an external appearance identical with that of the inspection subject region of said sample from a plurality of directions identical with those of the inspection subject region, thereby obtaining external appearance images of the comparison subject region picked up from the plurality of directions;

correcting mis-registrations between the external appearance images of the inspection subject region of said sample picked up from the plurality of directions and the external appearance images of the comparison subject region picked up from the plurality of directions that respectively correspond to the external appearance images of the inspection subject region picked up from the plurality of directions; and detecting defects of the inspection subject region by using the external appearance images of the inspection subject region of said sample picked up from the plurality of directions and the external appearance images of the comparison subject region picked up from the plurality of directions corrected in mis-registrations, wherein the step of detecting defects of the inspection subject region comprises the substeps of:

obtaining a difference image between a non-directional electron image obtained by picking up an image of the inspection subject region of said sample and a non-directional electron image obtained by picking up an image of the comparison subject region, by using local perturbation; and detecting defects of the inspection subject region by using information of the difference image obtained by using the local perturbation.

6. A defect inspection method comprising the steps of:

applying a focused electron beam onto a sample and conducting two-dimensional scanning on an inspection subject region;

detecting secondary electrons generated from an inspection subject region of said sample at the focused electron beam applying step by using a plurality of detectors, thereby obtaining a plurality of external appearance images of the inspection subject region of said sample;

picking up images of a comparison subject region designed so as to originally have an external appearance identical with that of the inspection subject region of said sample by using said plurality of detectors, thereby obtaining a plurality of external appearance images of the comparison subject region;

combining the plurality of external appearance images of the inspection subject region of said sample to form a first synthetic image and combining the plurality of external appearance images of the comparison subject region to form a second synthetic image;

obtaining a mis-registration quantity between the formed first synthetic image and the formed second synthetic image;

correcting mis-registrations between the plurality of external appearance images of the inspection subject region of said sample and the plurality of external appearance images of the comparison subject region that respectively correspond to the plurality of external appearance images of the inspection subject region, based on the obtained mis-registration quantity; and detecting defects of the inspection subject region by using the plurality of external appearance images of the inspection subject region of said sample and the plurality of external appearance images of the comparison subject region corrected in the mis-registrations.

7. The defect inspection method according to claim 6, wherein at the step of obtaining external appearance images of the inspection subject region of said sample, the plurality of external appearance images of the inspection subject region of said sample comprise two perspective images obtained by picking up an image of the inspection subject region of said sample from each of two opposed directions, and a non-directional electron image, and the plurality of external appearance images of the comparison subject region comprise two perspective images obtained by picking up an image of the comparison subject region from each of two opposed directions, and a non-directional electron image.

8. The defect inspection method according to claim 6, wherein the step of correcting the mis-registrations comprises the substeps of:

mixing two perspective images obtained by picking up an image of the inspection subject region of said sample from each of two opposed directions with a non-directional electron image, thereby synthesizing a first mixed image;

mixing two perspective images obtained by picking up an image of the comparison subject region of said sample from each of the two opposed directions with a non-directional electron image, thereby synthesizing a second mixed image; and comparing the first mixed image with the second mixed image, thereby obtaining mis-registration quantities respectively between the two perspective images and the non-directional electron image of the inspection subject region of said sample and the two perspective images and the non-directional electron image of the comparison subject region.

9. A defect inspection method comprising the steps of:

applying a focused electron beam onto a sample and conducting scanning;

picking up images of an inspection subject region of said sample from a plurality of directions, thereby obtaining a plurality of external appearance images of the inspection subject region;

picking up images of a comparison subject region designed so as to originally have an external appearance identical with that of the inspection subject region of said sample from a plurality of directions, thereby obtaining a plurality of external appearance images of the comparison subject region;

detecting defects of said sample by using the plurality of external appearance images of the inspection subject region and the plurality of external appearance images of the comparison subject region;

classifying the detected defects;

displaying the classified defects on a screen, wherein the step of detecting said defects comprises the substeps of:

correcting mis-registrations between the plurality of external appearance images of the inspection subject region and the plurality of external appearance images of the comparison second region; and detecting defects by comparing the plurality of external appearance images of the inspection subject region and the plurality of external appearance images of the comparison subject region corrected in the mis-registrations, wherein the step of correcting the mis-registrations comprises the substeps of:

mixing two perspective images obtained by picking up an image of the inspection subject region of said sample from each of two opposed directions with a non-directional electron image, thereby synthesizing a first mixed image;

mixing two perspective images obtained by picking up an image of the comparison subject region of said sample from each of the two opposed directions with a non-directional electron image, thereby synthesizing a second mixed image;

comparing the first mixed image with the second mixed image, thereby obtaining mis-registration quantities respectively between the two perspective images and the non-directional electron image of the inspection subject region of said sample and the two perspective images and the non-directional electron image of the comparison subject region; and correcting mis-registrations respectively between the two external appearance images and the non-directional electron image of the inspection subject region of said sample and the two external appearance images and the non-directional electron image of the comparison subject region, based on the obtained mis-registration quantities.

10. A defect inspection method comprising the steps of:

picking up images of a first region of a sample from a plurality of directions, thereby obtaining a plurality of external appearance images of the first region;

picking up images of a second region of said sample from a plurality of directions, thereby obtaining a plurality of external appearance images of the second region;

correcting mis-registrations between the plurality of external appearance images of the first region and the plurality of external appearance images of the second region;

detecting defects of said sample by using the plurality of external appearance images of the first region and the plurality of external appearance images of the second region corrected in the mis-registrations;

classifying the detected defects; and storing information concerning the classified defects, wherein the step of correcting the mis-registrations comprises the substeps of:

mixing two perspective images obtained by picking up an image of the first region of said sample from each of two opposed directions with the image obtained by picking up an image from the different direction, thereby synthesizing a first mixed image;

mixing two perspective images obtained by picking up an image of the second region of said sample from each of two opposed directions with the image obtained by picking up an image from the different direction, thereby synthesizing a second mixed image;

comparing the first mixed image with the second mixed image, thereby obtaining mis-registration quantities respectively between the two perspective images and the image obtained by picking up an image from the different direction of the first region of said sample and the two perspective images and the image obtained by picking up an image from the different direction of the second region of said sample; and correcting mis-registrations respectively between the two perspective images and the image obtained by picking up an image from the different direction of the first region of said sample and the two perspective images and the image obtained by picking up an image from the different direction of the second region, based on the obtained mis-registration quantities.

11. A defect inspection method comprising the steps of:

picking up images of a first region of a sample from a plurality of directions, thereby obtaining a plurality of external appearance images of the first region;

picking up images of a second region of said sample from a plurality of directions, thereby obtaining a plurality of external appearance images of the second region;

correcting mis-registrations between the plurality of external appearance images of the first region and the plurality of external appearance images of the second region;

detecting defects of said sample by using the plurality of external appearance images of the first region and the plurality of external appearance images of the second region corrected in the mis-registrations;

classifying the detected defects; and storing information concerning the classified defects, wherein the step of detecting said defects uses, information of a difference image two perspective images obtained by picking up an image of the first region of said sample from each of two opposed directions, and information of a difference image of two perspective images obtained by picking up an image of the second region from each of two opposed directions.

12. A defect inspection method comprising the steps of:

picking up images of a first region of a sample from a plurality of directions, thereby obtaining a plurality of external appearance images of the first region;

picking up images of a second region of said sample from a plurality of directions, thereby obtaining a plurality of external appearance images of the second region;

transmitting data of the plurality of external appearance images of the first region of said sample and data of the plurality of external appearance images of the second region of said sample;

detecting defects of said sample by using the transmitted plurality of external appearance images of the first region of said sample and the transmitted plurality of external appearance images of the second region of said sample; and classifying the detected defects, wherein the step of detecting said defects uses, information of a difference image of two perspective images obtained by picking up an image of the first region of said sample from each of two opposed directions, and information of a difference image of two perspective images obtained by picking up an image of the second region from each of two opposed directions.

13. A defect inspection apparatus comprising:

electron beam irradiation unit for irradiating an inspection target with an electronic beam focused thereon in a scanning manner;

a detection unit including a pair of narrow angle electron detectors and a non-directional electron detector, the narrow angle electron detectors detecting in narrow angle directions which are different from each other, electrons generated from the inspection target which is irradiated with the electron beam focused by the electron beam irradiation unit;

an imaging unit for imaging a pair of detection signals detected by the pair of narrow angle electron detectors of the detection unit to produce a pair of perspective images, and for imaging a detection signal detected by the non-directional electron detector to produce a secondary electron image; and an image processing unit for processing respective images of a defect portion and a reference portion of the inspection target which are imaged through the imaging unit by detecting the defect portion and the reference portion through the detection unit so as to detect a defect position of the inspection target;

wherein the image processing unit calculates a difference image of each of the pair of perspective images of the respective defect and reference portions, and detects the defect position of the inspection target from the calculated respective difference images between the defect and reference portions; and wherein the image processing unit calculates a difference image concerning the calculated respective difference images between the defect and reference portions, calculates a difference image between the calculated difference image of the defect portion and the calculated difference image of the reference portion, calculates a difference image of the secondary electron image between the defect portion and the reference portion, and detects the defect position of the inspection target from the calculated difference image between the defect portion and reference portion and the calculated difference image of the secondary electron image between the defect portion and the reference portion.

* * * * *